United States Patent [19]

Marsili

[11] Patent Number: 4,898,938

[45] Date of Patent: Feb. 6, 1990

[54] METHOD FOR PREPARING CRYSTALLINE CEFADROXIL MONOHYDRATE

[75] Inventor: Leonardo Marsili, Segrate, Italy

[73] Assignee: Rifar S.r.L., Milan, Italy

[21] Appl. No.: 80,999

[22] Filed: Aug. 3, 1987

[51] Int. Cl.$^4$ .................. C07D 501/22; A61K 31/545
[52] U.S. Cl. ..................................................... 540/230
[58] Field of Search ............................... 540/230, 222

[56] References Cited

U.S. PATENT DOCUMENTS 4,234,721  11/1980  Bouzard et al. ........................ 544/30
4,504,657  3/1985  Bouzard et al. ...................... 540/230

Primary Examiner—Nicholas S. Rizzo
Attorney, Agent, or Firm—Oblon, Spivak, McClelland, Maier & Neustadt

[57] ABSTRACT

The invention relates to a method for preparing crystalline cefadroxil monohydrate.

According to such a method a cefadroxil solvate is slurried with isopropyl alcohol containing less 6% to 18% of water at a temperature between +45° to +55° C.: the crystalline cefadroxil monohydrate is isolated by filtration.

Some of the cefadroxil solvates which can be used are novel: they are prepared by adding dimethylacetamide, N-methyl-2-pyrrolidone or monomethylformamide to an aqueous solution of cefadroxil at a pH between 5.5 and 6.

2 Claims, No Drawings

METHOD FOR PREPARING CRYSTALLINE CEFADROXIL MONOHYDRATE

The present invention relates to an effective method for preparing crystalline cefadroxil monohydrate.

Cefadroxil is a well known antibiotic substance having antibacterial activity: it is disclosed and claimed in the U.S. patent no. 3,489,752 according to which it is obtained by acylation of 7-ADCA with a amino-protected derivative of D (-)-alpha-p -hydroxyphenylglycine. U.S. Pat. No. 3,985,741 discloses preparation of cefadroxil by acylation of 7-ADCA with mixed anhydride of D-(-)-alpha-p-hydroxyphenylglycine when the latter's alpha-amino group has been blocked with a beta-keto compound such as methyl acetoacetate: the reaction mixture is first added with water and then with dimethylformamide to precipitate a crystallized solvate of cefadroxil having more than 3% of water content which, after filtration, is slurried in 90% methanol. In this connection it is to be noted that the so obtained cefadroxil crystals have a high methanol content, what is pharmaceutically unacceptable because such alcohol is toxic.

U.S. Pat. No. 4,504,657 describes and claims a different form of cefadroxil, which is the crystalline cefadroxil monohydrate having a well defined X-ray diffraction pattern characterizing said compound: this crystalline cefadroxil monohydrate is obtained (see also the U.S. patent RE 31,730) by acylation of silylated 7-ADCA with D(-)-alpah-p-hydroxyphenylglycine chloride hydrochloride. The reaction mixture is added first with water and then with dimethylformamide to precipitate the dimethylformamide solvate which after filtration is treated with water or a water/solvent mixture to cleave the solvate and to precipitate the desired final compound.

While all known methods for transforming the 7-ADCA into the mentioned aqueous solution containing cefadroxil can be used, the isolation technique is important. For instance, the cefadroxil aqueous solution can be prepared following the procedures described in Example XVI of the European patent application no. 001, 133, or in Examples 1 and 2 of the U.K. patent application no. 2,064,511 or in Examples 1 to 4 of the U.S. Pat. No. 4,234,721.

According to U.S. Pat. No. Re 31,730 and U.S. Pat. No. 4,234,721, the crystalline cefadroxil monohydrate is prepared by slurrying the cefadroxil DMF solvate with water or a water/solvent mixture. If water alone is used, the obtained product contains impurities as it is confirmed by what is written in lines 41-44 of col. 8 of Re 31,730: moreover the yield is low.

The U.S. Pat. No. Re 31,730 suggests therefore (Col. 8, lines 41-44) that the use of a mixture water/organic solvents (including alcohols) is preferred: in such a case the preferred water/solvent ratios are 1:3 or 1:1 (col. 8, lines 48-54; Examples 5 and 10; claim 19). However, in such conditions, an important amount of the desired final compound remains dissolved in the mother liquor and must be then recovered, as it is confirmed by what was written in the U.S. Pat. No. 4,234,721, col. 10, lines 3-8, and in the U.S. Pat. No. Re. 31,730, col 9, lines 62-68 to col 10, lines 1-4.

It has now been surprisingly found that if the cefadroxil solvate is slurried with a mixture water: isopropyl alcohol 6:94 to 18:82 by volume, the mother liquors contains a very small or no amount of cefadroxil: moreover the crystalline cefadroxil monohydrate precipitates in a very pure form, what appears to be due to the very low amount of water used.

Attempts have been made to use other alcohols, but the results have been not encouraging: indeed, if ethyl alcohol is used, the defadroxil molecule is decomposed; if methanol is used, the molecule of the final cefadroxil retains an exceedingly high amount of the same methanol, what is unacceptable in consequence of its toxicity: other alcohols have given unsatisfactory results.

It has been also found that, in addition to the known cefadroxil DMF solvate, also other novel cefadroxil solvates can be used, which are the cefadroxil solvates of dimethylacetamide, of N-methyl-2-pyrrolidone and of monomethylformamide.

Consequently the present invention concerns a method for producing crystalline cefadroxil monohydrate, according to which a cefadroxil solvate is slurried with isopropyl alcohol containing from about 6% to 18% of water, at a temperature in the range of about +45° C. to +55° C. and for a time between 1 to 2 hours, the crystalline cefadroxil monohydrate being then isolated by filtration.

The cefadroxil solvate can be a solvate of dimethylactamide, of N-methyl-2-pyrrolidone and of monomethylformamide which can be prepared by adding to an aqueous solution of cefadroxil just obtained from 7-ADCA a solvent selected from the group consisting of dimethylacetamide, N-methyl-2-pyrrolidone, monomethylformamide, while controlling the pH of the solution in the range 5.5-6, to give the corresponding cefadroxil solvate which precipitates and is filtered off.

The following Examples are given by way of illustration of the present invention in which the NMR spectra were recorded in D2O solution (15 mg/ml) on a Varian XL-300 spectrometer.

EXAMPLE 1

(Cefadroxil Dimethylacetamide Solvate

7-ADCA (45 g) was added to methylene chloride (700 ml) at room temperature. Triethylamine (35.5 g) was added over 15' with stirring at a temperature below 25° C. Trimethylchlorosilane (43.2 g) was then dropped over a 30' period. The mixture was stirred at 30° C. for 90' and then cooled to −10° C.

Dimethylaniline (31 g) and D(-)-p-hydroxyphenylglycyl chlorise hydrochloride hemidioxane solvate (63 g) were added and the mixture was stirred at −5° C./0° C. for about 90'. Water (170 ml) was added and the reaction mixture was stirred for 30'. The aqueous phase was diluted with dimethylacetamide (350 ml) and the pH was adjusted to 6.0 by slowly adding diethylamine at 25° C. The mixture was stirred at 20° C. for 120'. The cefadroxil dimethylacetamide solvate was collected by filtration, washed with dimethylacetamide/water 2:1 then with acetone to yield, after drying at 40° C., 81.3 g of the title compound

K.F.: 0.51%

HPLC Assay: 69.3% on dry basis

PMR: 6.9–7.35 $\delta$ (m,C$_6$H$_4$—); 5.59$\delta$[d, C(7)—H]; 5.15 $\delta$ (s,CH—CO); 4.98 $\delta$[d, CH—S];3.02–3.42$\delta$(m, S—CH$_2$); 1.8$\delta$(s, CH$_3$) characteristic of cefadroxil moiety and the following peaks due to the solvent:

2.83–3.01$\delta$(s,s, N(CH$_3$)$_2$); 2.04$\delta$(dd,COH$_3$)

$^{13}$C—NMR: 21.07$\delta$[CH$_3$—C=]; 30.93$\delta$[CH$_2$—S]; 58.78$\delta$[CH—NH$_2$]; 59.51 [CH—S]; 61.16 $\delta$[NH—CH—C—CO]; 124.60 $\delta$[C—CH$_3$]; 126.11 $\delta$[C—COOH];

166.21 δ[C, B-lactam]; 172.37δ[COOH]; 172.58 δ[CO—NH];129.05 δ, 132.7 δ, 118.99 δ, 160.45δ[aromatic carbon atmos] characteristic of Cefadroxil moiety and the following peaks due to the solvent: 23.15δ[CO—CH3]; 37.93δ[N—CH3]; 40.85δ[N—CH3]; 176.74δ[CO].

EXAMPLE 2

Cefadroxil Dimethylacetamide Solvate

Potassium methyl Dane salt of D(-)-p-hydroxyphenylglycine (30.3 g) was added to acetone (170 ml) and the mixture was cooled to −40° C. Ethylchlorocarbonate (11.15 g) and N-methylmorpholine (0.25 ml) were added at −40° C. The temperature was kept at −35° C. for 120' and then the mixture was cooled to −55° C.

7-ADCA (21.5 g) was charged at +5° C. into water (50 ml) and dimethylsuphoxide (90 ml) and triethylamine (11.3 g) were added. The obtained solution was cooled to 0° C. and the suspension of mixed anhydride (at −55° C.) was added to the solution of 7-ADCA.

The mixture was stirred at −25° C. for 60'; the temperature was raised to 0° C. and HCl 37% was added slowly during 60' to a constant pH 1.8. Methylene chloride (175 ml), was added and the mixture was stirred for 15'. The upper layer was diluted with didmethylacetamide (170 ml) and acetone (70 ml), the pH was adjusted to 6.5 at 0° C. with triethylamine. The mixture was stirred at 0° C. for 2 hours. The solvate was washed with dimethylacetamide/water 2:1 and then with acetone to yield 40.5 g of the title compound after drying at 40° C.

K.F.: 0.63%
HPLC Assary: 69.1% on dry basis

EXAMPLE 3

Cefadroxil Monomethylformamide Solvate

7-ADCA (30 g) was added to methylene chloride (450 ml), trimethylchlorosilane (28.8 g) was added and the mixture was stirred for 10'. Triethylaine (23.7 g) was then dropped over a 30' period while temperature was allowed to reach 30° C. The mixture was stirred 2 hours at 30° C. and then cooled to −10° C.

Bis-trimethyl-silyl-urea (21 g) and D(-)-p-hydroxyphenylglycyl chloride hydrochloride hemidioxane solvate(45 g) were added and the mixture was allowed to react at −5° C. for 90. After additional 30' stirring at 0° C., water (115 ml) was added.

The reaction mixture was stirred for 30', the aqueous layer cooled to 5° C. and diluted with monomethylformamide (240 ml). Triethylamine was added slowly over 60' and the pH was adjusted to 5.7 at 20° C. After stirring for 2 hours the slurry was filtered, the filter cake waashed with monomethylformamide/water 2:1 and then with acetone to yield, after drying at 40° C., 49 g of the title compound:

K.F.: 0.9 %
HPL Assay: 79.8% on dry basis
PMR: besides the peaks characteristic of Cefadroxil moiety shown in example 1, the following peaks are due to the solvent 7.98δ[s, HCO]; 2.71δcis [s, NHCH3]
13C-NMR: besides the peaks characteristic of Cefadroxil moiety shown in Example 1, the following peaks are due to the solvent: 27.07δ; 167.6δ[H—CO].

EXAMPLE 4

Cefadroxil 1-Methyl-2-pyrrolidone Solvate

7-ADCAA (30 g) was reacted according to the procedure described in Example 1 using 1-methyl-2-pyrrolidone instead of dimethylacemide.

Yield: 52 g
K.F.: 0.85%
HPLC Assay: 68.7% on dry basis
PMR: besides the peaks characteristic of Cefadroxil moiety shown in Example 1, the following peaks are due to the solvent 3.45 [t. CH2]; 2.36δ[t, CH2(3)]; 1.98δ[q, CH2(4)]; 2.84δ[s,N—CH3)].
13C-NMR: besides the peaks characteristic of Cefadroxil moiety shown in example 1, the following peaks are due to the solvent: 19.71δ[CH2)]; 32.27δ[N, CH3]; 33.45δ[CH2(3)]; 52.97δ[CH2(5)]; 180.84δ[C (2)].

EXAMPLE 5

Crystalline Cefadroxil monohydrate

Cefadroxil dimethylacetamide solvate (40 g) prepared according to example 1 was slurried in isopropyl alcohol (200 ml) containing 13% of water at 50° C. for 90'. The mixture was cooled to +5° C. and cefadroxil monohydrate was collected to yield 28.5 exhibiting the same X-ray diffraction pattern of an authentic sample of crystalline cefadroxil monohydrate.

K.F. 4.7%
HPLC Assay: 98.4% on dry basis.

EXAMPLE 6

Crystalline Cefadroxil monohydate

Cefadroxil 1-methyl-2-pyrrolidone solvate (30 g) prepared according to example 4 was slurried in isopropyl alcohol (150 ml) containing 10 ml of water at 50°-52° C. for 120'.

The mixture was cooled to +5° C. and then filtered. Crystalline cefadroxil monohydrate was collected to yield 20.9 g
K.G. 4.9%
HPLC Assay: 98.1% on dry basis.

EXAMPLE 7

Crystalline Cefadroxil monohydrate

Cefadroxil monomethylformamide solvate (50 g) prepared according to example 3 and having K.F. 1.4% was slurried in isopropyl alcohol (250 ml) containing 40 ml of water at 48° C. for 150'. The mixture was cooled to +2° C. and crystalline cefadroxil monohydrate was collected.

Yield: 40.8 g
K.F.: 5.2%
HPLC Assay: 99.2% on dry basis.

Proceeding as above indicated but using Cefadroxil dimethylformamide solvate instead of monomethylformamide solvate the same final compound has been obtained.

I claim:

1. A method for preparing crystalline cefadroxil monohydrate which comprises slurrying a cefadroxil solvate with isopropyl alcohol containing from about 6% to about 18% of water, at a temperature in the range of about +45° C. to +55° C. for a time of about 1 to 2 hours, and isolating the crystalline cefadroxil monohydrate by filtration.

2. The method according to claim 1, wherein said cefadroxil solvate is a solvate of dimethylacetamide, N-methyl-2-pyrrolidone or monomethylformamide, and which is prepared by adding to an aqueous solution of cefdroxil obtained from 7-ADCA, a solvent selected from the group consisting of dimethylacetamide, N-methyl-2-pyrrolidone and monomethylformamide, while controlling the pH of the solution in the range of about 5.5–6, to give the corresponding cefadroxil solvate which precipitates and is filtered off.

* * * * *